United States Patent [19]
Kraft et al.

[11] Patent Number: 4,809,707
[45] Date of Patent: Mar. 7, 1989

[54] ELECTRODE FOR NON-INVASIVE ALLERGY TESTING

[75] Inventors: Thomas L. Kraft, Houston; Howard A. Vick, Missouri City; James W. Meador, Houston, all of Tex.; Corrine Johnson, executrix of said Howard A. Vick, deceased

[73] Assignee: KVM Engineering, Inc., Houston, Tex.

[21] Appl. No.: 722,772

[22] Filed: Apr. 12, 1985

[51] Int. Cl.$^4$ .......................................... A61M 37/00
[52] U.S. Cl. .................................. 128/736; 128/743; 604/20
[58] Field of Search ............... 128/736, 743, 664, 640, 128/798, 803, 419 R; 604/20

[56] References Cited

U.S. PATENT DOCUMENTS

| | | | |
|---|---|---|---|
| 2,235,436 | 3/1941 | Laub | 128/743 |
| 2,298,506 | 10/1942 | Parker | 128/743 |
| 2,301,536 | 11/1942 | Morse | 128/743 |
| 2,304,817 | 12/1942 | Grozin | 128/743 |
| 3,699,813 | 10/1972 | Lamb | 128/736 |
| 4,135,514 | 1/1979 | Zaffaroni et al. | 604/894 |
| 4,141,359 | 2/1979 | Jacobsen et al. | 604/20 |
| 4,148,005 | 4/1979 | Larsen et al. | 128/736 |
| 4,211,222 | 7/1980 | Tapper | 604/20 |
| 4,214,592 | 7/1980 | Jacquet et al. | 128/743 |
| 4,312,332 | 1/1982 | Zick | 128/635 |
| 4,402,311 | 9/1983 | Hattori | 128/736 |
| 4,474,570 | 10/1984 | Ariura | 128/798 |
| 4,509,531 | 4/1985 | Ward | 128/736 |

FOREIGN PATENT DOCUMENTS

| | | | |
|---|---|---|---|
| 2826391 | 1/1980 | Fed. Rep. of Germany | 128/736 |
| 2076963 | 12/1981 | United Kingdom | 128/664 |

OTHER PUBLICATIONS

"The Use of Differential Skin Temperature Measurements in the Evaluation of Post Traumatic Oedema Control" by H. Hambury et al., Med. & Biol. Eng., vol. 13, No. 2, pp. 202-208.

"Performance of a Spin Evaporimeter" by A. E. Wheldon et al; Med. & Biol. Eng. & Comput., Mar. 1980, vol. 18, pp. 201-205.

*Primary Examiner*—Lee S. Cohen
*Assistant Examiner*—David Shay
*Attorney, Agent, or Firm*—Tim L. Burgess

[57] ABSTRACT

Disclosed herein is an electrode for performing a plurality of allergy tests on a patient undergoing tests. The allergy electrode consists of a plurality of individual testing electrodes and a single common electrode. Each of the testing electrodes includes allergen delivery apparatus and a temperature sensor. The allergen is contained in a removable allergen impregnated pad. If a dry allergen is used, it may be hydrolized with a drop of distilled water prior to application. A small electric charge charges a charge plate on one side of the allergen pad and a common ring on the electrodes is grounded in circuit with the charging plate, thereby causing electric field to transfer the allergen through the pores of the skin. The area surrounding the allergen delivery area is sensed for temperature by a thin film temperature sensor and a rigid temperature conducted base. A thermistor or other temperature to voltage transducer converts the sensed temperature to an electric voltage which is applied through appropriate differential amplifiers and multiplexer to an analog to digital converter. The digital data is then stored by a microprocessor in random access memory. An output device can be connected to receive the stored data and the time at which it was stored so as to manifest to the physician the change in temperature of the tested area with respect to time.

34 Claims, 2 Drawing Sheets

ELECTRODE FOR NON-INVASIVE ALLERGY TESTING

This invention relates to an electrode for allergy testing and more particularly an electrode of the type for non-invasively providing an allergen transcutaneously into the patient's body and thereafter automatically determining whether an allergic reaction has occurred and the degree of any such reaction.

Testing for allergies has been the standard medical technique for many years. In recent years it has become more important as many patient disorders have been found to be based on some type of allergic response. Traditionally, testing for allergies have included the traditional skin test and more recently the RAST test. The traditional skin test is exemplified by either a scratch test or a needle injection test. In either case, the skin is fractured and an allergen substance of the allergy being tested is placed on the skin puncture. Where an allergic reaction occurs, the area around the puncture swells and turns a reddish color. Generally, the degree of the allergic reaction is measured by measuring the diameter of the wheal or red mark on the skin. However such measurement is only semi quantitative in that different reactions quantitatively do not generate sufficient differences in the diameter of the wheal in all instances. The RAST test is widely used where the allergy is a IgE mediated allergy. This type of test is very expensive and is performed on the blood serum.

Both of the prior art types of testing have several draw backs. First and foremost with respect to the traditional skin test some patients risk infection, undergo great pain and even can go into shock as a result of an allergic reaction to the injected allergen. This risk can of course be reduced by utilizing very small amounts of allergen, but then many allergic reactions will not occur. Thus, it will be necessary to perform the traditional skin test a multitude of times with increasing amounts of allergen. Such a solution is both expensive and painful to the patient as well as time consuming. Other disadvantages of course, are the pain the patient suffers generally both as a result of the testing procedure due to puncturing the skin as well as the resulting allergic reaction wheal which is formed.

It is known in the prior art that each allergic reaction wheal causes a slight rise in the skin temperature in the area of the wheal. Thermographic techniques have been used in the past to diagnose an allergic reaction in certain patients. However, these tests have not been entirely satisfactory because quantitative results are not available since the thermography technique can only detect the presence or absence of an allergic reaction. In addition, a significant investment in large equipment is necessary in order to perform the thermography. Lastly, the same pain and over reaction disadvantages exist as in the traditional testing procedures. Such a thermographic technique is described in the Journal of Clinical Immunology, November 1972, Vol. 50, No. 5 by Chintana Sphipatonakul, M.D. and Raymond G. Slavin, M.D., both of Saint Louis, Mo.

It would be preferable to eliminate many of these risks, undesirable pain and expense, as well as to generate a more reliable qualitative determination of the degree of the allergic reaction.

In accordance with one aspect of this invention there is provided an electrode for measuring temperature dependent reactions on the skin of the patient comprising a base, and temperature pick up means affixed to the base at a position adapted to be placed in contact with the skin. In addition, the electrode includes transducer means juxtaposed to the temperature pick up means for converting the temperature of the pick up means to an electric signal and electric lead means coupled to the transducer means and adapted for electrical connection to processor means for carrying the electric signal manifesting the skin temperature to the processor means for processing.

In accordance with another aspect of this invention there is provided an allergen delivery system for transcutaneously delivering an allergen to a patient undergoing allergy testing comprising means for containing an allergen, one side of which is adapted to contact the skin of the patient and a charge plate contacting the other side of said allergen containing means. In addition the system includes means for providing an electric charge to the charge plate, whereby the allergen transcutaneously delivered to the patient.

One preferred embodiment of the present invention is hereafter described with specific reference being made to the following figures, in which.

Figure 1:
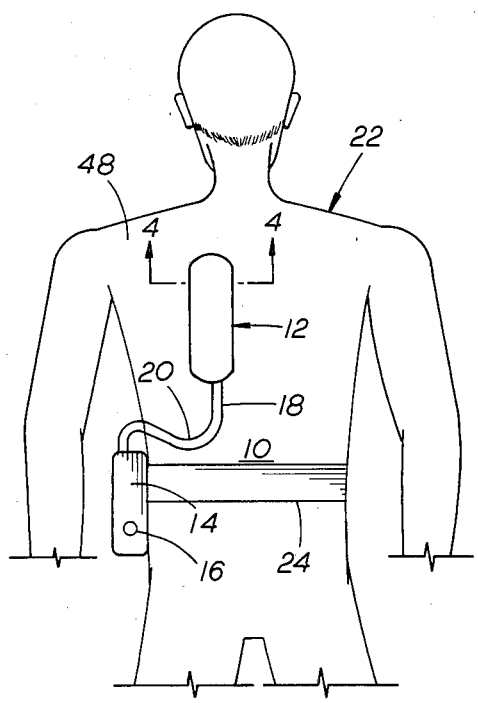
FIG. 1 shows the allergy testing system of the present invention attached to the back of the patient.

Referring now to FIG. 1, allergy testing system 10 is shown as including an allergy testing electrode 12 and allergy testing unit 14. Unit 14 includes a start switch 16 and is coupled to electrode 12 by a temperature sensing lead 18 and a charging lead 20. Electrode 12 may be placed at any convenient place on a patient 22 such as the back as shown in FIG. 1 or the arm or other areas on which it is desired to perform an allergy test. Electronic unit 14 may be held around the patient's waist by a belt 24 or may rest in the patient's lap.

As will be explained in more detail hereafter, electrode 12 is prepared and placed on patient 22 at the desired place. Wires 18 and 20 are then connected to electronic unit 14 and switch 16 is depressed. The patient is then sent to the waiting room to wait. Approximately fifteen minutes later, the testing is completed and unit 14 is disconnected from electrode 12 and returned to the doctor. Electrode 12 is then removed from the patient and the test is concluded. Thereafter, an output means may be coupled to unit 14 to provide the results of the test to the physician for review.

Figure 2:
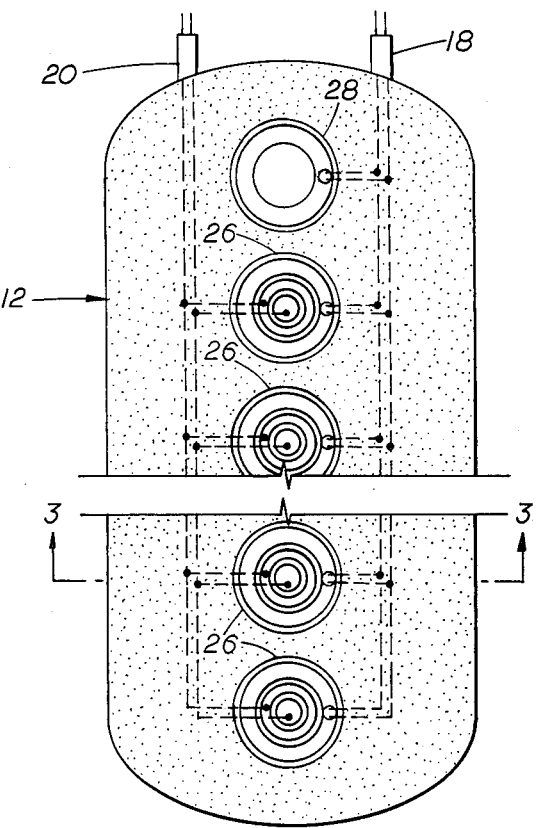
FIG. 2 shows a enlarged view of the bottom of the allergy testing electrode.

Referring now to FIG. 2, the bottom side of electrode 12 is shown. The bottom side is that side which is placed directly against the skin of patient 22. Electrode 12 includes a plurality, for instance eight, of allergy testing electrodes 26 and a single common electrode 28. Each of the allergy testing electrodes 26 includes both means for delivering an allergen transcutaneously to the patient and temperature sensing means for sensing the skin temperature in the area surrounding the position where the allergen was delivered. Common electrode 28 only includes means to sense the temperature of the skin in an area where no allergen was delivered; thus, common electrode 28 senses the normal skin temperature of patient 22. Each of the allergy testing electrodes 26 and common electrodes 28 are connected to both leads 18 and 20. Lead 18 may be a plurality of individual wires, a different one of which is coupled to each of the electrodes 26 and 28 in a manner to be described in more detail hereafter. Lead 20 consists of two wires, one of which is at ground and the other of which carries a positive voltage. Both of the wires of lead 20 may be coupled to each of the allergy testing electrodes 26.

Figure 3:
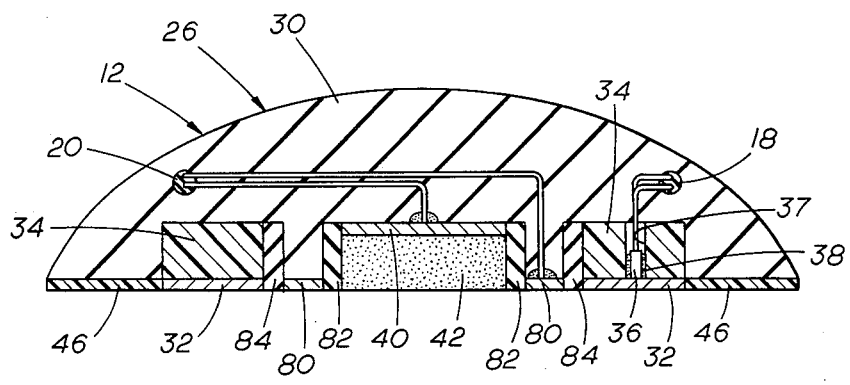
FIG. 3 shows a view taken across lines 3—3 of FIG. 2.

Referring now to FIG. 3, the detailed construction of one embodiment of the allergy testing electrodes 26 is shown, it being understood that each of the other electrodes 26 is substantially identical in construction. Each of the electrodes 26 is contained in a common housing 30, which is a part of electrode 12. Housing 30 may be a generally soft material and is both an electrical and thermal insulator. On the bottom of electrode 26 a thin film thermal equilibrium ring 32 is positioned within a thermally insulating base 34. Both ring 32 and base 34 may be annular rings having a center opening therein. Ring 32 is selected to be a type which can withstand the effects of solvents such as alcohol, generally associated with testing. It further should be a type which can have materials soldered, welded, or bonded thereto. It has been found that ceramic, platinum alloys and stainless steel are sufficient for this purpose. Base 34 may be any of a variety of well known heat insulating plastic materials. Base 34 should be generally rigid so to adequately support the thin film temperature equilibrium ring 32. Ring 32 may be either vacuum deposited over base 34 or may be an integral member secured thereto by gluing or other adhesive techniques.

A thermister 36 is soldered or fastened conductively to ring 32 through a hole 37 in base 34. A bonding material 38 such as electrically insulating and thermally conducting epoxy, is placed within the hole 37 to thermally bond thermister 36 with ring 32. The solder also thermally bonds thermister 36 with ring 32. A pair of leads from wire 18 is coupled to the leads from thermister 36. As is well known in the art a thermister is a type of resistor which has a decreasing resistance as the temperature of the surrounding area increases. Thus a thermister can be coupled in circuit with other electronic components and a signal can be generated having a voltage proportional to the temperature of the surrounding area. It also is possible to replace thermister 36 with a thermocouple which operates by providing a voltage based on the difference in temperature between the two ends thereof.

A charge plate 40 and removable allergen pad 42 are placed within the center opening of the annular ring 32 and base 34. Also within the center opening of ring 32 is an annular ring negative electrode 80, electrically insulated from charge plate 40 and pad 42 by annular ring insulator 82 and from ring 32 by annular ring insulator 84. Charge plate 40 is coupled to the voltage carrying wire from charging lead 20 and negative electrode 80 is coupled to the ground lead of wire 20. A charge of between 1.0 and 4.0 milliamperes may be provided over lead 20 to charge allergen pad 42. Allergen pad 42 may be a porus material into which a dry allergen is impregnated. Prior to use, a drop of distilled water may be placed on allergen pad 42 to hydrolize pad 42. When pad 42 is placed in contact with the skin of patient 22 and plate 40 receives a charge from lead 20, the allergen contained within pad 42 is transcutaneously delivered beneath the skin of patient 22. An electric field is established between charge plate 40 and negative electrode 80. This electric field penetrates through the skin of patient 22 as it flows from plate 40 to electrode 80. The charged allergen molecules migrate through the pores of the skin as the electric field traverses the skin. It should be noted that it is unnecessary to create any break in the skin of the patient 22 using the technique of allergen delivery.

Pad 42 may be made removable from the area in which it is shown. In such case, electrode 12 may be continually reused for testing by merely placing new pads 42 with the desired allergen therein.

The edges of electrode 12 are covered with a double sided tape 46 which can be used to affix electrode 12 to the desired area on patient 22. Tape 46 may be specially fabricated to fit over all non-electrode areas shown in FIG. 2 of electrode 12 so that each of the electrodes 26 and 28 are firmly attached against the skin of patient 22.

Figure 4:
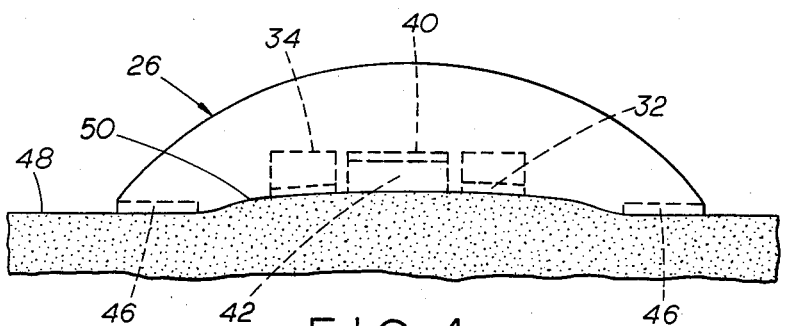
FIG. 4 shows a view taken across line 4—4 of FIG. 1.

Referring now to FIG. 4, after the allergen has been transcutaneously delivered to the skin of patient 22, a reaction will occur if the patient is allergic to the allergen. As seen in FIG. 4, the skin 48 of the patient 22 swells to a wheal 50 in the area of the reaction. Wheal 50 may be a slight puffiness or reddening of the skin and generally increases in temperature. It has been found that the greater the temperature increase the greater the reaction. Further, the greater the reaction, the larger the size of wheal 50 and the brighter the redness in wheal 50. In FIG. 4, the sensor ring 32, and charge plate 40 and allergen pad 42 have been shown in dashed lines to show their positioning with respect to wheal 50. From Figuire 4 it is seen that the increased temperature of the skin 48 at wheal 50 can be sensed by sensor ring 32. The temperature profile of the wheal is such that the temperature maximum occurs at the center and tapers lower radially outward. The position of thermister 36 is at the shoulder of the temperature curve. Hence it is important for ring 32 to be low in mass and high in temperature conductivity, so as to reach an equilibrium point.

This temperature can be converted to an electrical signal by thermistor 36 and applied over the leads of lead 18 to electronic unit 14. A similar sensing of a normal skin temperature occurs at common electrode 28 which provides a signal over the wires of lead 18 to electronic unit 14 manifesting a normal skin temperature. By applying both signals to a differential amplifier, the difference in temperature can be easily obtained. By taking the measurement at periodic intervals, not only can the difference in temperature be obtained, but the change in temperature over time can be indicated. Thus, the physician utilizing the allergy testing system 10 can determine the degree of reaction by looking at how fast and how high the temperature rises. In order to avoid any contributive infra-red heating imparted by the electric fields created to drive the allergen into the skin, the field should be completed before the thermal measurements are taken. Alternatively, the field may be cycled on and off during the test and measurements taken during the off times. For example, the field may be on for one minute out of five and thermal readings taken during the four minute off time.

The physician can also utilize various ones of the allergy testing electrodes 26 shown in FIG. 2 for the same allergy test by putting different concentrations of the same allergen in various pads 42 and inserting them in different allergy testing electrodes 26. By doing this the physician can see the rate of increase of the reaction for different concentrations of allergen and can make a better diagnosis as to the treatment of the patient. Further, by retaining the record of the data, the physician can modify treatment as necessary by continually testing the patient's reaction at different times during the term of the treatment.

For slow reacting allergens, the physician may instruct the patient to wear the device for many hours. After a period prescribed by the physician, the unit 14, can be returned to the physician for analysis and diagnosis. This unique capability has not previously been possible.

Figure 5:
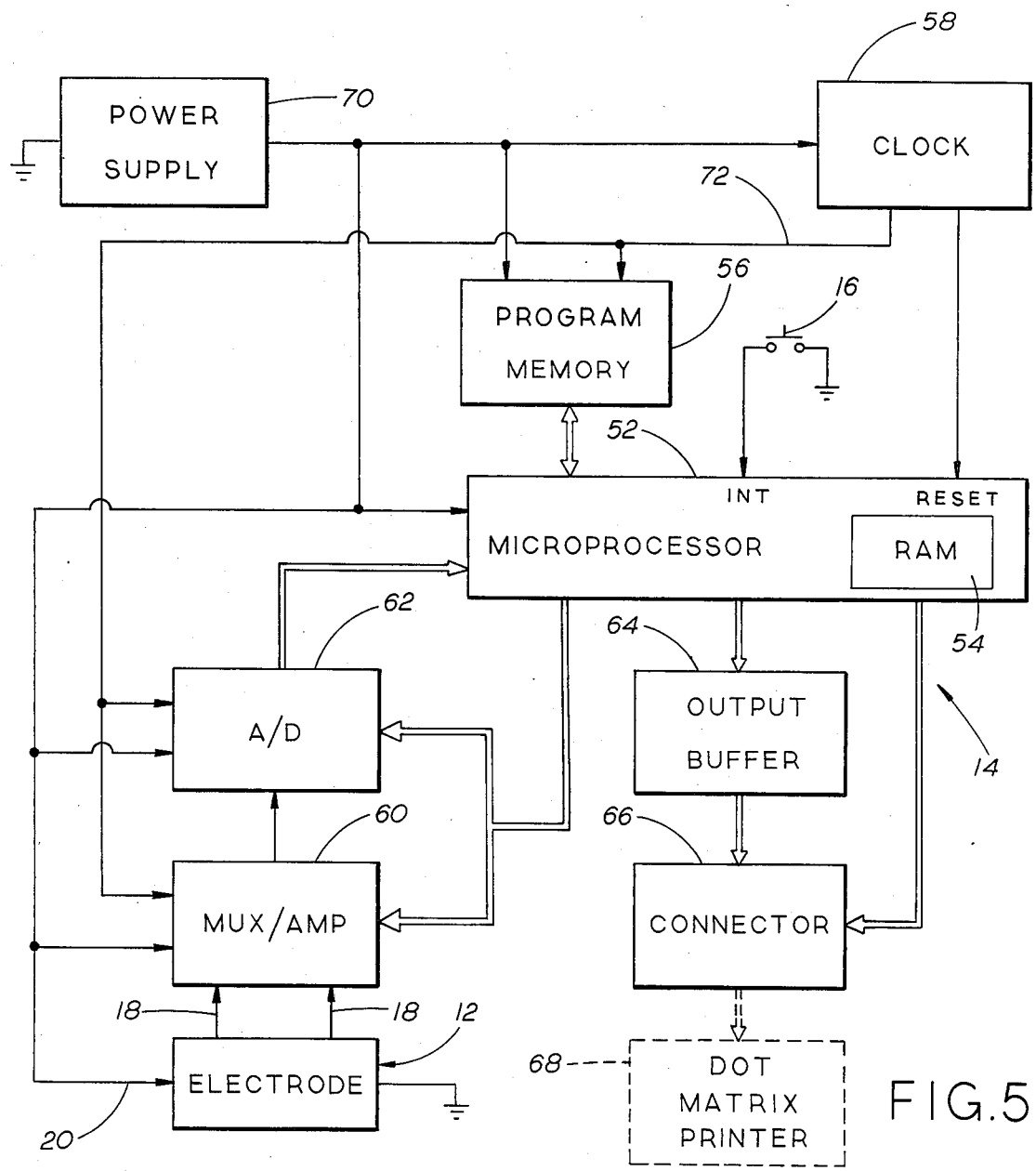
FIG. 5 shows a block diagram of the electronic system used in conjunction with the electrode of the subject invention.

Referring now to FIG. 5, a block diagram of electronic unit 14 is shown. The heart of electronic unit 14 is a microprocessor 52 which contains therein onboard random access memory (RAM) 54. Attached to microprocessor 52 in a conventional manner is program memory 56 which may be contained in a read only memory (ROM). Switch 16, shown in FIG. 1, is coupled to the interupt (INT) input of microprocessor 52 to initiate the action of microprocessor 52. Depression of switch 16 causes microprocessor 52 to make predetermined number, e.g. thirty, skin temperature readings from each of the eight testing electrodes 26 during the testing period, e.g. the next fifteen minutes. The exact time of each of the readings is determined by a clock 58 which has one input coupled to the RESET input of microprocessor 52.

Each of the nine pairs of wires of lead 18 are provided from electrodes 12 to multiplexer/amplifier (MUX-/AMP) 60. Multiplexer/amplifier 60 may consist of one differential amplifier each having a lead from common plate 44 attached as one input thereof and a different one of the leads from an electrode 26 attached as the other input thereof. The output of each of the differential amplifier will be a signal the amplitude of which manifests the difference in temperature of an area under test to the normal skin temperature and those areas. Where there is very little or no reaction, the amplitude of such a signal would be very low, whereas for those areas where a significant allergic reaction occurs, the amplitude of the signal will be much greater.

The multiplexer portion of multiplexer/amplifier 60 is controlled by microprocessor 52 to select one of the electrode signals as the differential amplifier input signals and provide the difference as an output of multiplexer/amplifier 60. The output selected from multiplexer/amplifier 60 is provided an analog input to analog to digital converter 62 which converts the analog voltage provided thereto in it to a digital signal which in turn is provided to microprocessor 52. Microprocessor 52 then notes the time at which the signal is provided and stores it in an appropriate place in random access memory 54.

After all of the data has been obtained by microprocessor 52, and stored in memory 54, it can be extracted from microprocessor 52 through output buffer 64 and connector 66. Output buffer 64, for instance, may be connected to one of the input/output ports of microprocessor 54 and connector 66 may have the output of buffer 64 as well as certain control signals from microprocessor 52 connected thereto. An output device, such as a dot matrix printer 68, may be connected to connector 66 to print the data output from RAM 54. Alternatively, a terminal display unit may be connected to connector 64 or any other type of output means which is capable of displaying the data in a fashion desirable to the physician.

Power supply 70 is used to provide power to each of the various units in electronic unit 14. In addition, power supply 70 provides the electric charge over lead 20 to the charge plate 40 in the allergy testing electrodes 26 and to the negative annular ring 80 of each electrode. Because electronic unit 14 is desired to be portable, power supply 70 typically will be a battery. In order to conserve energy a second signal is provided from clock 58 which lasts for the duration of each of the individual test readings. This may only be a few milliseconds in length. During the provision of the second signal over lead 72 from clock 58, e.g. the analog to digital converter 62 and the multiplexer/amplifier 60 are energized; during other periods of time they are de-energized so that they do not draw additional power from power supply 70. The same signal over lead 72 is also applied to de-energize program memory 56 except during the critical time during which testing is done. By selecting the components contained in electronic unit 14 to be constructed of CMOS fabrication technology, a minimum drain on power supply 70 occurs except during the period of testing. As previously indicated, this testing period occurs only for a few milliseconds every thirty seconds. By selecting power supply 70 to be a lithium type battery commonly used in cardiac pacemakers, the life of electronic unit 14 can be many years.

A more detailed description of electronic unit 14 and the technique of diagnosing the allergic reaction is given in commonly assigned U.S. patent Ser. No. 722,798 filed Apr. 12, 1985 now abandoned.

What is claimed is:

1. An allergy testing system comprising:
   means for containing a hydrolyzed allergen, such means having opposed first and second surfaces, said first surface being adapted to contact an area of skin of a person being tested;
   a charge plate contacting said second surface of said allergen containing means;
   means for providing an electric charge produced from an electric current of between 1 and 4 milliamperes to said allergen, whereby said allergen is transcutaneously delivered into said area of skin; and
   means effectively positioned for detecting the temperature of said area of skin proximate said allergen containing means and for outputting an electric signal indicative of said temperature.

2. The invention according to claim 1 wherein said allergen containing means is removeable from said system.

3. The invention according to claim 2 wherein said allergen containing means is porous.

4. The invention according to claim 1 wherein said system further includes a return electrode positioned to contact the skin of said patient, said return electrode having an opening therein in which said allergen containing means and said charge plate are positioned, said charge plate and allergen containing means being electrically insulated from said return electrode.

5. The invention according to claim 4 wherein said return electrode is coupled serially in circuit with said patient, said allergen containing means and said charge plate, and through which circuit said current flows.

6. The invention according to claim 5 wherein said allergen containing means is removable from said system.

7. The invention according to claim 6 wherein said allergen containing means is porous.

8. An allergic response testing device for skin, including:
   iontophoretic allergen delivery means for transcutaneously delivering a selected substance into the skin of a person to test for allergic response of the person to said substance, said means including charging and return electrodes positioned for spaced topical placement on the skin effective to provide a conductive iontophoretic path through the tissue of the skin, said charging electrode including a charging member and in electrical communication therewith a medium for containing said selected substance, said medium being positioned to separate said charging member from contact with the skin upon said topical placement of said charging electrode; and
   temperature sensing and signaling means coupled with said allergen delivery means and positioned for placement in thermal contact with said skin at an area in juxtaposition to said path, for sensing skin temperatures in said area after initiation of said transcutaneous substance delivery and for outputting electric signals indicative of such temperatures.

9. The device of claim 8 in which said temperature sensing and signaling means includes thermal pickup means for sensing the temperature of the said area of skin and transducer means in thermal communication with said pickup means for converting said communicated sensed temperature into an electrical output signal.

10. The device of claim 9 in which said transducer means is a thermister.

11. The device of claim 9 including a base, said allergy delivery means and said temperature sensing and signaling means being insulatively affixed to said base, said pickup means being laterally disposed to one of said electrodes.

12. The device of claim 9 in which said pickup means surrounds said allergy delivery means.

13. The device of claim 9 in which said charging and return electrodes respectively include charging and return electric lead means for delivery respectively of charging current and return current, and wherein said temperature sensing and signaling means includes signaling electric lead means for delivering said output electric signal.

14. The device of claim 9 in which said medium is a replaceable pad.

15. The invention of claim 9 further including a second thermal pickup means and a second transducer means positioned remote from said thermal pickup means and transducer means and from skin effects caused by the delivery of said allergen by said allergen delivery means, to provide a signal manifesting a normal temperature of said skin of said person.

16. The invention according to claim 9 further including a plurality of associated thermal pickup means, transducer means and allergen delivery means.

17. The invention according to claim 16 further including normal temperature measuring means positioned to be remote from the skin effects caused by the delivery of said allergen by said allergen delivery means.

18. The invention according to claim 17 further including means to removably affix said device to said skin.

19. The invention according to claim 13 in which said temperature sensing and signaling means includes thermal pickup means for sensing the said temperature and a thermister in thermal communication with said pickup means, said thermal pickup means surrounding said allergen containing means.

20. A device for performing a plurality of allergy tests on the skin of a person under test comprising:
   a plurality of testing means each including:
      a temperature pickup and signal providing means having an opening therethrough adapted to be placed in contact with the skin of said person, said pickup and signal providing means providing an electric signal manifesting the temperature of said skin contacting said pickup and signal providing means, and
      allergen delivery means positioned through said opening for transcutaneously delivering said allergen to said patient, said delivery means including electrode means across which voltage may be impressed to generate an electric field and allergen containing means positioned to be in the generated electric field and adapted to contact said skin;
   common temperature sensing means, adapted to be placed in contact with said skin in an area remote from any reaction caused by the transcutaneous delivery of said allergen to said patient, for providing an electric signal manifesting the normal temperature of said skin; and
   lead means coupled to each of said testing means and said common means for providing an electric charge to said electrode means and for receiving said signal from said pickup and signal providing means and said common means.

21. The invention according to claim 20 wherein said allergen delivery means includes an allergen impregnated pad having opposed first and second surfaces, said first surface being positioned to contact said skin; a charge plate contacting said second surface of said pad; and a return electrode electrically insulated from said charge plate and said pad and positioned to contact said skin, each of said charge plate, pad and return electrode being within said opening.

22. The invention according to claim 20 wherein said device further includes a housing material containing each of said testing means, said common means and said lead means, said housing material being a temperature and electrical insulating material.

23. The invention according to claim 20 wherein each of said temperature pickup and signal providing means includes a temperature conductive ring and a temperature to electric signal transducer means thermally coupled to said ring.

24. The invention according to claim 23 wherein said transducer means is a thermistor.

25. The invention according to claim 23 wherein said ring is a thin film member affixed to a rigid temperature conductive base.

26. The invention according to claim 25 wherein said transducer means is thermally bonded to said base.

27. The invention according to claim 26 wherein said transducer means is a thermistor.

28. A method of testing for, and signaling indicia of, an allergic response manifested at the skin of a person, comprising
   (a) establishing and completing a conductive path in skin tissue between a charging electrode, which includes a substance to be tested for allergenicity, and a spaced apart return electrode, thereby to deliver such substance iontophoretically into the skin tissue; and (b) detecting the temperature of the skin proximate said path and outputting an electric signal indicative of said temperature.

29. The method of claim 28 in which step (a) is cyclically performed in repetitions of predetermined duration and step (b) is performed between each cycle of step (a).

30. A method of allergy testing, comprising:
placing a hydrolyzed allergen containing member in contact with an area of skin of a person being tested;
providing an electromotive-force to said member;
discontinuing said electro-motive force;
sensing the temperatures of the skin of the person proximate said member after said electromotive force is discontinued during a period of time effective for sensing the rate and extent of temperature rise in said skin in an allergic response of the person to said allergen;
transducing said sensed temperatures during said period to electric output indicia of said temperatures; and
signaling said electric output indicia during said period.

31. The method of claim 30 in which the steps of providing and discontinuing are cyclically performed in repetitions of predetermined duration of providing and the steps of sensing, transducing and signaling are performed between each of said steps of providing and discontinuing.

32. The method of claim 30 wherein said allergen containing member includes a first surface for contacting said skin of a person being tested and an opposed second surface for contacting a charge plate, and said step of providing includes positioning a charge plate on said second surface of said member and applying an electro-motive force to said charge plate.

33. The method according to claim 32 wherein said electro-motive force is applied by providing an electric current between 1.0 and 4.0 milliamperes to said charge plate.

34. The method according to claim 37 wherein said method includes utilizing an electrode having a permanent charge plate and a replaceable member, said method further including placing a new member in said electrode and attaching said electrode to said patient's skin for each test.

* * * * *